US010765659B2

(12) United States Patent
Tesse

(10) Patent No.: US 10,765,659 B2
(45) Date of Patent: Sep. 8, 2020

(54) POTENTIATED TULATHROMYCIN

(71) Applicant: SEPTEOS, Paris (FR)

(72) Inventor: Nicolas Tesse, Vaucresson (FR)

(73) Assignee: SEPTEOS, Paris (FR)

( * ) Notice: Subject to any disclaimer, the term of this patent is extended or adjusted under 35 U.S.C. 154(b) by 0 days.

(21) Appl. No.: 16/084,804

(22) PCT Filed: Mar. 14, 2017

(86) PCT No.: PCT/FR2017/050581
§ 371 (c)(1),
(2) Date: Sep. 13, 2018

(87) PCT Pub. No.: WO2017/158282
PCT Pub. Date: Sep. 21, 2017

(65) Prior Publication Data
US 2019/0091197 A1 Mar. 28, 2019

(30) Foreign Application Priority Data

Mar. 14, 2016 (FR) ...................................... 16 52110

(51) Int. Cl.
A61K 31/352 (2006.01)
A61K 31/7052 (2006.01)
A61K 31/7048 (2006.01)
A61P 31/04 (2006.01)

(52) U.S. Cl.
CPC ........ A61K 31/352 (2013.01); A61K 31/7048 (2013.01); A61K 31/7052 (2013.01); A61P 31/04 (2018.01)

(58) Field of Classification Search
None
See application file for complete search history.

(56) References Cited

U.S. PATENT DOCUMENTS

| 2014/0039045 A1 | 2/2014 | Reynolds | |
| 2016/0250167 A1* | 9/2016 | Strobel | A61K 47/44 424/93.5 |

FOREIGN PATENT DOCUMENTS

| DE | 19631037 A1 | 2/1998 |
| WO | WO 98/56802 A1 | 12/1998 |
| WO | WO 99/66796 A1 | 12/1999 |
| WO | WO 2006/120567 A2 | 11/2006 |
| WO | WO 2009/043987 A1 | 4/2009 |
| WO | WO 2012/001089 A1 | 1/2012 |
| WO | WO 2016/041958 A1 | 3/2016 |

OTHER PUBLICATIONS

Hendry et al., "Antimicrobial efficacy of eucalyptus oil and 1,8-cineole alone and in combination with chlorhexidine digluconate against microorganisms grown in planktonic and biofilm cultures," Journal of Antimicrobial Chemotherapy, vol. 64, 2009 (Advance Access publication Oct. 16, 2009), pp. 1219-1225.
International Search Report and Written Opinion of the International Searching Authority (Forms PCT/ISA/220, PCT/ISA/210 and PCT/ISA/237) for International Application No. PCT/FR2017/050581, dated May 30, 2017.
Jedličkova et al., "Antibacterial Properties of the Vietnamese Cajeput Oil and Ocimum Oil in Combination with Antibacterial Agents," Journal of Hygiene, Epidemiology, Microbiology and Immunology, vol. 36, No. 3, 1992, pp. 303-309.
Marinas et al., "Rosmarinus officinalis essential oil as antibiotic potentiator against *Staphylococcus aureus*," Biointerface Research in Applied Chemistry, vol. 2, Issue 1, 2012 (published online Feb. 15, 2012), pp. 271-276.
Mulyaningsih et al., "Synergistic properties of the terpenoids aromadendrene and 1,8-cineole from the essential oil of Eucalyptus globulus against antibiotic-susceptible and antibiotic-resisnant pathogens," Phytomedicine, vol. 17, No. 13, Nov. 1, 2010, pp. 1061-1066.

* cited by examiner

Primary Examiner — Dale R Miller
(74) Attorney, Agent, or Firm — Birch, Stewart, Kolasch & Birch, LLP

(57) ABSTRACT

The invention relates to enhanced tulathromycin for use in the treatment, metaphylaxis or prevention of a microbial infection, characterized in that a compound of formula (I) is used in combination with tulathromycin at a weight ratio compound of formula (I):microbial agent of 8:1 to 1:10, and in that the microbial infection is induced in particular by a strain A pathogen in which the concentration of compound (I) satisfies the following equation: $[C]<[MIC]/x$, where $[C]$ is the concentration according to the invention of compound (I) to be used in strain A, $[MIC]$ is the minimum inhibitory concentration measured for compound (I) alone in strain A, and x is at least 100, advantageously at least 1000, more advantageously between 2000 and 10,000, or even greater than 50,000.

16 Claims, 2 Drawing Sheets

POTENTIATED TULATHROMYCIN

The invention relates to compounds of formula (I), used at a dose at which they no longer have antimicrobial properties, for use as agents intended to potentiate the tulathromycin with which they are co-administered. In particular, the "potentiator(s)+tulathromycin" combination is aimed at preventing and/or treating bacterial and fungal infections in animals.

The invention also relates to a process for potentiating tulathromycin wherein a compound (or several compounds) of formula (I) is co-administered with tulathromycin. In this process, the compound of formula (I) is used at a dose at which it is inactive alone.

OBJECT OF THE INVENTION

Background

The invention aims to provide solutions to problems related to the decrease or loss of activity of antibiotics during their period of commercial and medical use.

Following the advent of antimicrobials in the 1940s, it quickly became apparent that microbes (bacteria and fungi) could adapt to the antimicrobials used. The efficacy of the latter decreases over time and with the extent of use. There are two strategies for controlling resistance: first, discovering new antimicrobial molecules; second, combining existing antimicrobials with molecules for selectively blocking mechanisms of resistance.

Over the past two decades, there has been a decrease in the number of new antimicrobial molecules entering the market, which has led to a major increase in the global prevalence of resistant microbes. The result is a complex situation for patients whose microbial infections are increasingly difficult to cure.

The Applicant has already demonstrated, in application PCT/EP2015/071093, that compounds of formula (I) are able to potentiate antibiotics. In this application, it was demonstrated that good in vitro results were confirmed in vivo. Application PCT/EP2015/071093 does not cite tulathromycin.

Tulathromycin is a macrolide antibiotic. Its chemical name (IUPAC nomenclature) is (2R,3S,4R,5R,8R,10R,11R,12S,13S,14R)-13-[2,6-dideoxy-3-C-methyl-3-O-methyl-4-C-[(propylamino)methyl]-α-L-ribo-hexopyrano-syl]oxy]-2-ethyl-3,4,10-trihydroxy-3,5,8,10,12,14-hexamethyl-11-[3,4,6-trideoxy-3-(dimethylamino)-β-D-xylo-hexopyranosyl]-oxy]-1-oxa-6-azacyclopentadecan-15-one. It is marketed by Zoetis under the brand name Draxxin® for treating cattle and pigs or other domesticated animals.

In cattle, tulathromycin is notably indicated for the treatment, metaphylaxis and prevention of bovine respiratory diseases associated with tulathromycin-sensitive *Mannheimia haemolytica, Pasteurella multocida, Histophilus somni* and *Mycoplasma bovis*. It is also indicated for the treatment and metaphylaxis of infectious bovine keratoconjunctivitis associated with tulathromycin-sensitive *Moraxella bovis*.

In pigs, tulathromycin is notably indicated for the treatment, metaphylaxis and prevention of porcine respiratory diseases associated with tulathromycin-sensitive *Actinobacillus pleuropneumoniae, Pasteurella multocida, Mycoplasma hyopneumoniae* and *Haemophilus parasuis*.

DESCRIPTION

The invention describes the use of compounds of formula (I) to potentiate tulathromycin. Unexpectedly, these compounds have demonstrated their ability to potentiate the effect of tulathromycin at low doses (from 0.01 to 100 mg/L) very far from those at which they can, alone, have antimicrobial properties. Consequently, the tulathromycin co-administered with compounds of formula (I) has, because of potentiation, higher activity than that usually observed.

It is important to remember that, in absolute terms, every molecule has antimicrobial properties. The antimicrobial properties of a molecule must therefore be assessed in comparison with the minimum concentration that inhibits the bacteria.

The invention is based on the surprising discovery that compounds with antimicrobial properties at very high doses (a level incompatible with medical use for this purpose) and with minimal inhibitory concentrations (MICs) above 5 000 mg/L, advantageously above 10 000 mg/L, have potentiating effects at low doses (0.01 to 100 mg/L). At these doses, it becomes possible to use compounds (I) in animals.

Also surprisingly, it was shown that the potentiating effect is better at low doses of compound (I), and that the effect (for compounds having antimicrobial properties at very high doses) increases when moving away from the dose at which compound (I) alone has antimicrobial properties.

For example, it was unexpectedly shown that cineole, which has antimicrobial properties at a concentration of the order of g/L (MIC of 25 000 mg/L to 50 000 mg/L, i.e. 2.5 to 5%, depending on the strains), has antibiotic-potentiating effects at these concentrations close to the MIC (1 to 3 dilutions).

When its concentration is decreased below the MIC, cineole no longer potentiates antibiotics (see Examples 2 and 6 of application PCT/EP2015/071093). Then, very surprisingly, it was shown that by further significantly decreasing the concentration of cineole, from 10 to 50 times less than the MIC, cineole again has potentiating effects on a very large number of antibiotics on a very large number of strains, this time at doses compatible with medical or veterinary use.

A great advantage is that compounds (I) used at these doses, far from their efficacy threshold, can usually be used in animals without toxicity constraints owing to the absence of toxicity or to acceptable levels of toxicity. This would not be the case if they were to be used at high doses at which they have antimicrobial properties or even at doses close to their MIC at which they could potentiate antimicrobials.

Equally surprisingly, the potentiating effect observed with the compound according to the invention is not specific to a particular resistance mechanism but is observed on various strains, regardless of whether they have developed or not one or more distinct mechanisms of resistance.

PRIOR ART

The prior art describes in numerous publications the antimicrobial properties of some compounds (I). These publications do not anticipate the potentiating effect of compounds (I) at doses far from their efficacy threshold.

The prior art is consequent on compounds (I) because they belong to chemical classes that have been studied extensively in many fields. Compounds (I) within the scope of the present invention have the following characteristics which allow them to be set apart from the prior art and which allow consideration of their use as potentiators of antimicrobials administered to humans and animals:

A/ They are used at low doses (0.01 to 100×) mg/L) far from their antimicrobial properties threshold; their potentiating effect is not specific to particular mechanisms of action or of resistance.

B/ They have been validated by screening methods adapted to their physicochemical characteristics.

C/ They have, at the doses at which they potentiate, an effect/toxicity ratio that allows safe use in humans or animals.

D/ They constitute one or more isolated chemical entities whose characteristics are reproducible constantly to infinity because the method by which they are obtained (synthesis, hemisynthesis, extraction) allows it.

E/ They have no particular toxicity that would prohibit their use even at low doses (genotoxicity, cardiotoxicity, etc.).

A/ Concerning the Activity Levels Measured in the Prior Art

In the prior art, the concentration used to observe antimicrobial activity is not compatible with prospective use in humans or animals, particularly during systemic application. In most scientific publications, medical use is contemplated whereas the effective concentrations measured (of the order of several mg/mL) are incompatible with this use. The antimicrobial effects measured have very often been for levels of essential oil, or the active compound thereof, of the order of several mg/mL. However, such a concentration is not suitable for prospective use in humans or animals, particularly systemically. One milligram per millilitre corresponds to 1 g/L or 1 g/kg or 0.10%. If the MIC was 1 mg/mL, it would be necessary, based on pharmacokinetic parameters, to administer at least 1 g/kg/d live weight. For example, the effective dose for a cow should be at least 500 g/d and at least 60 g/d for humans (this corresponds to the minimum dose because it is assumed here that the product is fully absorbed and distributed in the body). These doses are far too high to be considered for safe therapeutic use.

Examples include two publications that cite the antibacterial effect of terpenoids and their potential to potentiate antimicrobials:

Biointerface Vol 2, Issue 1, 2012, 271-276: Marinas et al.: *Rosmarinus officinalis* essential oil as antibiotic potentiator against *Staphylococcus aureus*.

If this publication seems close to the invention it is important to note the contemplated dose (p. 274) of eucalyptol which, at 25 µL/mL (or 25 mL/L or 25 g/L) is far from the dose that can be administered to humans or animals. The synergy test contemplated is carried out with the storage solution (50% cineole), i.e. 50 g/L, higher than the MIC of cineole in the publication, a dosage incompatible with medical use.

Journal of Antimicrobial Chemotherapy (2009) 64, 1219-1225: Hendry et al.: Antimicrobial efficacy of eucalyptus oil and 1,8-cineole alone and in combination with chlorhexidine digluconate against microorganisms grown in planktonic and biofilm cultures.

Here again, synergy is contemplated with a product that has antimicrobial properties. The concentration of cineole contemplated is 4 g/L, a dose very close to the MIC of cineole in the publication (8-64 g/L) but too high to be considered a possibility for human or animal administration.

The invention clearly differs from these two publications because in the latter the doses contemplated are very high whereas the concentration contemplated is close to the MIC.

B/ Concerning the Inadequacy of the Methods Described in the Prior Art

The authors who have worked via different approaches (active products only, natural products, etc.) on the chemical families comprising compounds (1) generally used standard methods for measuring antibacterial effect without adapting said methods to the hydrophobic and volatile nature of terpenoids and phenylpropanoids.

For example, WO 99/66796 (Wisconsin Alumni Research Foundation) describes a method for sensitizing microbial cells to antibacterial compounds comprising a step of contact with an antibacterial compound and a sesquiterpenoid, to enhance the effect of the antibacterial compound.

In this application, the MICs were determined using the agar diffusion method, which is inappropriate for the volatile and hydrophobic nature of compounds (I) and related families. This method consists of placing paper discs impregnated with known amounts of compounds to be tested on agar seeded with the bacteria to be studied. A concentration gradient of the compound around each disc is established on the agar; after 18 hours the diameter of the inhibition halo is measured. However, this method is not reliable for hydrophobic compounds which, due to very different surface tensions and contact angles on hydrophilic surfaces, interfere with the formation of the concentration gradient in the agar. In some areas, the concentration of compounds to be tested is much higher than the theoretical concentration. Thus, the tests cannot be quantitative, although they can be qualitative. Furthermore, the hydrophobic compound to be tested is diluted in ethanol, without however correcting the result even though ethanol is an antibacterial and volatile compound.

Note that this application teaches that no effect is obtained with terpenes other than sesquiterpenes.

C/ Concerning the Toxicity of the Compounds of the Prior Art

Regarding natural compounds and compositions, there is confusion between natural origin and absence of toxicity. Essential oils (and derivatives thereof) are usually described as having low toxicity, which is often true in food applications or in perfumery but incorrect in therapeutic administration.

Regarding isolated chemical compounds, confusion also exists and is based on the natural origin (extraction) of the compounds.

For example, WO2006/120567 (Advanced Scientific Developments) describes pharmaceutical compositions comprising at least one active therapeutic substance described as non-toxic, selected from carveol, thymol, eugenol, borneol, carvacrol, alpha-ionone, beta-ionone, and isomers, derivatives and mixtures thereof, and comprising an antibiotic as second active therapeutic substance. Carveol, thymol, eugenol, borneol, carvacrol, alpha-ionone and beta-ionone, used alone, have antibacterial activity and a number of them however also raise the question of toxicity, which is ignored in this application.

For example, the toxicity data for carvacrol is as follows: the $LD_{50}$ (mouse, intravenous) is 80 mg/kg while the lowest oral lethal dose is 100 mg/kg in two mammalian species (cat and rat). These data should be compared with the 0.3 mg/mL (or 300 mg/kg) dose contemplated in the document.

D/ Concerning the Chemical Variability of the Compounds Described in the Prior Art On an industrial scale, the use of essential oil is problematic in terms of quality and reproducibility given that the composition of an essential oil varies from batch to batch.

For example, DE 196 31 037 (Boehringer) describes the use of tea tree essential oil to potentiate the effect of antibiotics on *Staphylococcus aureus* strains. The main component of tea tree essential oil is terpinen-1-ol.

This variability has three consequences that limit industrial exploitation for an application in humans or animals:
  it is difficult to ensure consistency of therapeutic effect
  it is difficult to ensure low toxicity of the products supplying materials and managing the quality and reproducibility thereof is expensive.
The following table summarizes the teaching of these prior arts:

In contrast to the term "antimicrobial", which includes antibacterials and antifungals intended for administration, the term "biocide" includes products with antimicrobial properties intended for application to inert systems (viruses and prions).

"Antibacterial properties" and "antifungal properties" mean not only bactericidal and fungicidal properties characterized by the destruction of bacteria and fungi (and

TABLE 1

| | A/Active products at the dose contemplated | B/Screening method incompatible with the chemical nature of the compounds | C/Toxicity at the dose contemplated | D/Problem of chemical variability | Dose contemplated |
|---|---|---|---|---|---|
| Marinas et al. | Yes | Yes | Yes | No | 15 g/L i.e. 15 000 mg/L |
| Hendry et al. | Yes | No | Yes | No | 4 g/L i.e. 4 000 mg/L |
| WO 2009/043987 Aroma Technologies | Yes | Yes | Yes | Yes | 0.1 to 0.4% i.e. 1 to 4 000 mg/L |
| WO 2006/120567 Advanced | Yes | Yes, (no dispersant) | Yes | No | 0.3 mg/mL i.e. 3 000 mg/L |
| DE 196 31037 Boehringer | Yes | No (test in milk) | Yes | Yes | 1 to 2 mg/mL i.e. 1 000 to 2 000 mg/L |
| WO 99/66796 Wisconsin Alumni | Yes | Yes | Yes | No | 1 mM i.e. 222 mg/L (for sesquiterpenoids) |
| Present Invention | No | No | No | No | 0.01 to 100 mg/L |

The work relating to compounds (I) at low doses far from those at which they have antimicrobial activity is novel and the prior art has not, to our knowledge, contemplated this use.

Definitions

Figure 1:
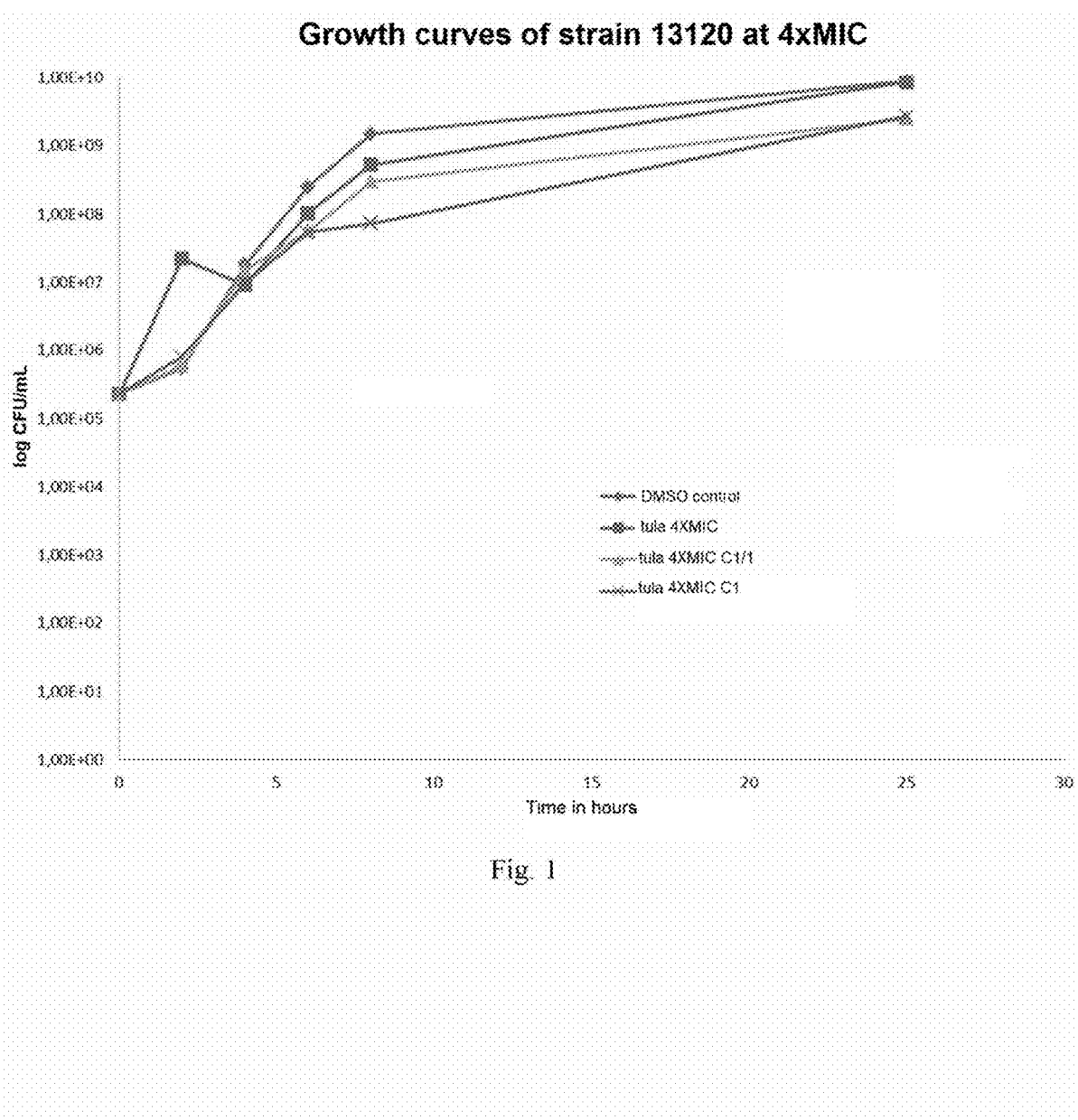
FIG. 1 is the results of the growth test on strain 13120 (*E. coli*).

"Microorganism" means any living organism that is invisible to the naked eye because of its small size.

"Organism" means any animal or plant biological entity (living being) capable of being born, developing and normally reproducing.

In this patent, the definition of microbe adopts the definition of microorganism, limited to the medical field to which the invention relates. Thus "microbes" are potentially pathogenic living microorganisms (bacteria, fungi, yeast and mycobacteria). The term therefore excludes inert pathogens such as viruses and prions.

"Antimicrobial" means any compound, intended to be administered to humans or animals, capable of killing or inhibiting microbial growth. Pharmaceutically acceptable salts of these antimicrobials are also included in this definition. This includes, for example, salts of sodium, potassium, calcium, etc., and amine salts of procaine, dibenzylamine, ethylenediamine, ethanolamine, methylglucamine, taurine, etc., as well as acid addition salts such as hydrochlorides and basic amino acids. The term thus includes antibiotics (combinations thereof with resistance mechanism inhibitors), antifungals intended for systemic or local use.

"Antimicrobial properties" means the properties of any substance capable of destroying or inhibiting microbial growth. Products with antimicrobial properties notably include antimicrobials and biocides.

yeasts, mycobacteria), but also bacteriostatic and fungistatic properties characterized by inhibition of the growth of said bacteria and fungi (and yeasts, mycobacteria). Products with antibacterial or antifungal properties notably include antimicrobials.

For the purposes of the present invention, "antibiotic-resistant bacterium" means a bacterium resistant to at least one, notably at least two, in particular at least three, or even at least four, conventionally used antibiotic(s) or antibiotic family(ies).

For the purposes of the present invention, "multi-resistant bacterium" means a bacterium resistant to several antibiotics, in particular to which the strain should be sensitive, or a priori sensitive, more particularly a bacterium which has at least two non-natural resistances.

A distinction is made between "natural resistances" and "acquired resistances". Some antibiotics have never been effective, in non-toxic doses, against certain bacterial strains or species. This is a natural resistance. When normally effective antibiotics prove to have little or no efficacy against a bacterium, this bacterium has developed acquired resistance.

For the purposes of the present invention, "microbial infection" means an infection caused by one or more microbial strains and includes the phases from host colonization to the pathological phases. The expression "microbial infection" therefore includes any harmful effect, clinical sign, symptom or any disease occurring in humans or animals as a result of colonization by the microbe.

According to the invention, "terpenoid" means any compound comprising a backbone close to a terpene. "Terpene" refers to an isoprene derivative obtained biologically by condensation of $C_5$ units, leading for example to monoterpenes, sesquiterpenes. "Close to" means that the backbone is similar to a terpene or different in that at least one alkyl substituent, normally present, may be absent or attached to another atom. The backbone may also be substituted by various radicals such as saturated or unsaturated, linear or cyclic aliphatic radicals (alkyl, alkenyl, alkylenes), oxy, aldehydes, esters, alcohols, ethers, or the sulphur- or nitrogen-containing equivalents thereof. The terpenoid may advantageously be of natural origin.

According to the invention, "phenylpropanoid" means any compound comprising a backbone close to a phenylpropane. "Phenylpropane" refers to a derivative obtained by biosynthesis from phenylpropane and leading to $C_6$ (aromatic)-$C_3$ (aliphatic) or $C_6$ (aromatic)-$C_1$ (aliphatic) derivatives and to the corresponding lactones. "Close to" means that the backbone is similar to a phenylpropane, in particular the phenyl unit is present, or is different in that at least one alkyl substituent, normally present, may be absent or attached to another atom. The backbone may also be substituted by various radicals such as saturated or unsaturated, linear or cyclic aliphatic radicals (alkyl, alkenyl, alkylenes), oxy, aldehydes, esters, alcohols, ethers, or the sulphur- or nitrogen-containing equivalents thereof. The phenylpropanoid may advantageously be of natural origin.

The term "prophylaxis" or "prevention of infection" as used in the present application means any degree of delay in the onset of clinical signs or of symptoms of infection, as well as any degree of inhibition of the severity of clinical signs or symptoms of infection, including, but not limited to, the total prevention of said infection. This requires that the antimicrobial and the compound according to the invention be co-administered to humans or animals likely to be colonized by a microbial strain as a preventive measure, for example following a surgical procedure, implantation of a medical device, an intrusive medical procedure. This prophylactic administration may take place before, during or after the procedure likely to cause an infection (especially a nosocomial infection) with the aim of preventing, improving, and/or reducing the severity of any subsequent infection.

For the purposes of the present invention, the term "treatment" implies that the antimicrobial and the compound according to the invention are co-administered to a subject (human or animal) at the time of colonization or after contamination or suspicion of contamination by a microbial strain likely to cause an infection such as a nosocomial infection. The term "treatment" or "treating an infection" therefore includes:
  any curative effect (inhibiting the growth of, or destroying, the microbe) obtained by virtue of co-administration of the antimicrobial+compound according to the invention as well as both improvement in the clinical signs or symptoms observed and improvement in the subject's condition.
  slowing, interrupting and stopping the progression of infection. Co-administration of the antimicrobial-compound according to the invention can also slow the progression of a microbe and/or completely or partially prevent a microbial infection from spreading to surrounding tissues and beyond.
  inhibition, attenuation or prevention of harmful consequences of infection such as cellular or physiological damage caused by toxins produced by certain microbes in infected or surrounding tissues.

The term "metaphylaxis", as used in the present application, refers to any preventive and systematic treatment of animals that are presumed healthy but are at risk.

The term "co-administered" means that the tulathromycin and the compound according to the invention (or the mixture of compounds according to the invention) are administered in combined or juxtaposed form to the subject. The combination includes any drug combination, any pharmaceutical composition, any pharmaceutical kit, and any drug comprising (i) at least tulathromycin and (ii) at least one compound according to the invention. Compounds (i) and (ii) may be present in the form of a mixture or in the form of separate formulations or compositions in said combination. The combination may also comprise several compounds according to the invention, in particular two or three or more compounds according to the invention. The combination may also comprise one or more other antibiotics. These components form a functional unit due to a common indication, which is the implementation of an antimicrobial treatment. This combination therapy is more specifically intended for the prophylaxis and/or treatment of infections and diseases of microbial origin, in particular nosocomial infections.

The co-administration may be simultaneous or spread over time.

The term "simultaneous" means that the tulathromycin and the compound according to the invention (or the mixture of compounds according to the invention) are administered together, at the same time, to a subject. These compounds may be administered in the form of a mixture or, simultaneously but separately, in the form of separate compositions.

The expression "sequential administration" means that the tulathromycin and the compound according to the invention (or the mixture of compounds according to the invention) are administered not simultaneously but separately over time, one after the other.

The term "to potentiate" tulathromycin means that the use of a compound according to the invention produces a prophylactic, metaphylactic or therapeutic effect superior to the prophylactic, metaphylactic or therapeutic effect obtained by using tulathromycin alone. This can be expressed in different, alternative or cumulative ways: increasing the effect of tulathromycin, decreasing the dose of tulathromycin at constant effect of tulathromycin, reducing MIC. Furthermore, the potentiation allows the development of resistance to be minimized or even eliminated.

The expression "increasing the effect of tulathromycin" means broadening the microbial spectrum of tulathromycin activity, increasing the speed of action of tulathromycin, improving the clinical success (cure rate) or the speed of clinical success (time to cure) of tulathromycin, at constant dose of tulathromycin.

The expression "decreasing the amount of tulathromycin used" means that the use of compounds according to the invention allows the use of a smaller amount of tulathromycin than the amount of tulathromycin normally necessary to obtain a given therapeutic, metaphylactic or prophylactic effect when tulathromycin is administered alone. The decrease in the amount of tulathromycin used may be more or less substantial; it is preferably at least 10%, and more preferably at least 20%, even more preferably at least 410%, or even 50% or more compared to the amount normally necessary to obtain a given therapeutic or prophylactic effect.

"MIC" means "minimal inhibitory concentration", which is the lowest concentration of substance at which microbial growth is no longer observed after 18 to 24 hours of contact under conditions favourable to microbial growth.

The minimum inhibitory concentration measurement tests are performed in a solid agar medium according to current international standards (CLSI standards M7-A9 January 12): dispersion of the compounds to be tested in Mueller Hinton agar. An adaptation relating to the hydrophobicity of the compounds and compositions is however necessary to disperse them in the medium: the compounds are diluted in a solvent. The compounds and compositions incorporated in the agar may be first diluted in one or more solvents (Tween® 80 diluted in water, Tween@ 80 diluted in propylene, DMSO diluted in water). The medium may be cation-adjusted. The strains are deposited on the surface of the agar with a Steers apparatus. In the examples, various methods for dissolving the products are tested in parallel to circumvent problems related to the water/solvent distribution coefficient of the molecules (antimicrobial and potentiator) as the bacteria grow only in the aqueous phase. The technical constraint will not affect the in vivo tests. The same dilution methods can be used in liquid media (microplates and tubes). The same methodology is used with fungi.

$MIC_{50}$ and $MIC_{90}$ represent the concentrations that inhibit 50% and 90% in number of strains of the same genus, respectively.

A product with a genotoxic effect is a product that shows a deleterious effect on genetic material.

Genotoxicity can be measured by the Ames test, in particular according to the guidelines of the International Conference on Harmonisation (ICH).

For the purposes of the present invention, "halogen atom" means fluorine, chlorine, bromine and iodine atoms.

For the purposes of the present invention, "heteroatom" means N, O or S, advantageously O.

For the purposes of the present invention, "$(C_1-C_6)$alkyl" group means a linear or branched saturated monovalent hydrocarbon chain containing 1 to 6, preferably 1 to 4, carbon atoms. Examples include methyl, ethyl, propyl, isopropyl, butyl, isobutyl, sec-butyl, tert-butyl, pentyl or hexyl.

For the purposes of the present invention, "$(C_2-C_6)$alkenyl" group means a linear or branched monovalent hydrocarbon chain containing at least one double bond and containing 2 to 6 carbon atoms. Examples include ethenyl or allyl groups.

For the purposes of the present invention. "$(C_1-C_6)$haloalkyl" means a $(C_1-C_5)$alkyl group, as defined above, wherein one or more hydrogen atoms have been replaced by a halogen atom as defined above. In particular, it may be a $CF_3$ group.

For the purposes of the present invention, "$(C_1-C_6)$alkoxy" group means a $(C_1-C_6)$alkyl group as defined above, linked to the rest of the molecule via an oxygen atom. Examples include methoxy, ethoxy, propoxy, isopropoxy, butoxy and tert-butoxy.

For the purposes of the present invention, "$(C_2-C_6)$alkenoxy" group means a $(C_2-C_6)$alkenyl group, as defined above, linked to the rest of the molecule via an oxygen atom. An example is the group —$OCH_2CHCH_2$.

For the purposes of the present invention, "$(C_1-C_5)$alkylene" or "$(C_1-C_6)$alkanediyl" group means a linear or branched divalent hydrocarbon chain containing 1 to 6 carbon atoms, such as, for example, a methylene, ethylene, propylene, butylene, pentylene or hexylene group.

For the purposes of the present invention, "$(C_2-C_6)$alkenylene" or "$(C_2-C_6)$alkenediyl" group means a linear or branched divalent hydrocarbon chain containing 2 to 6 carbon atoms and at least one double bond, such as, for example, a vinylene (ethenylene) or propenylene group.

DESCRIPTION OF THE INVENTION

The invention relates to tulathromycin potentiated by a compound of formula I for use in the treatment, metaphylaxis and prevention of microbial infection. It therefore relates to a combination of tulathromycin and a compound having the following formula I:

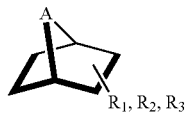

wherein $R_1$, $R_2$, $R_3$ each independently represent H, OH, a $(C_1-C_6)$alkyl, $(C_2-C_6)$alkenyl, $(C_1-C_6)$haloalkyl, $(C_1-C_6)$alkoxy, $(C_2-C_6)$alkenoxy, $(C_1-C_6)$haloalkoxy, —O—CO—$(C_1-C_6)$alkyl group:

A represents a heteroatom or an R-(Het)-R' or -(Het)-R group wherein R. R' each independently represent a $(C_1-C_4)$alkanediyl group optionally substituted by $C_1-C_4$ alkyl radicals and Het represents a heteroatom. A advantageously represents a -(Het)-R group in a compound of formula (I):tulathromycin mass ratio varying from 8:1 to 1:10.

The compound of formula (I):tulathromycin mass ratio varies more advantageously from 4:1 to 1:10, more advantageously from 1:1 to 1:10, even more advantageously from 1:1 to 1:5.

This means that the administered dose of compound of formula (I) is of the same order of magnitude as that of tulathromycin.

The mass ratio is the ratio of doses in mg/kg of the compound and of tulathromycin to be administered to humans or animals.

Surprisingly, it was shown that the potentiating effect decreases when the dose of compound according to invention (or mixture of compounds according to invention) increases. This potentiating effect may reappear at the MIC of the compound alone, but this is not the object of the invention.

In the context of the present invention, in vitro, the concentration of inactive compound, at which a potentiating effect is observed, is very far from the threshold of antimicrobial properties (MIC), when antimicrobial properties are observed. "Very far" means that the in vitro concentration is at least 10 times, advantageously at least 20 times, more advantageously at least 50 times, even more advantageously at least 100 times, lower than the MIC.

In particular, on a pathogenic strain A which induces the microbial infection concerned, the concentration of compound (1) advantageously satisfies to the following equation:

$$[C]<[MIC]/x$$

Where [C] is the concentration according to the invention of compound (I) to be used on strain A

[MIC] is the MIC measured for compound (I), alone, on this strain A x is greater than or equal to 100, advantageously to 1 000, more advantageously x is between 2 000 and 10 000, or even greater than 50 000.

In vitro, the doses of compound (I) are less than 100 mg/L, advantageously less than 64 mg/L, more advantageously between 0.01 and 25 mg/L, even more advantageously between 1 and 16 mg/L.

In the administered compositions, the concentration, per unit dose per kilogram, of compound of formula (I) is advantageously less than 100 mg, more advantageously less than 64 mg.

Compounds (I) can be used at low concentrations (in vitro at concentrations of the order of µg/mL) to potentiate tulathromycin, which is fully compatible with prospective use in animals (particularly if systemic administration is desired).

This makes it possible to contemplate doses in animals of less than 64 mg/kg, advantageously between 0.01 and 64 mg/kg, more advantageously between 0.1 and 30 mg/kg, even more advantageously between 0.5 and 10 mg/kg.

The potentiating compound according to the invention is advantageously administered at a concentration such that its maximum serum concentration is less than 250 mg/L, advantageously less than 150 mg/L, more advantageously between 10 and 150 mg % L, after administration.

Of course, at these concentrations, the compound can be administered to animals, including systemically, and has no major adverse effects, in particular carcinogenicity or genotoxicity.

In general, compounds of formula (I) have no genotoxic effect.

It is interesting to note that cineole is present on the list of substances authorized under the European regulation on maximum residue limits (Commission Regulation 37/2010 of 22 Dec. 2010).

Tulathromycin is advantageously administered at a dose of less than 64 mg/kg, advantageously between 0.01 and 64 mg/kg, more advantageously between 0.1 and 30 mg/kg, even more advantageously between 0.5 and 10 mg/kg.

For tulathromycin, in cases where it is usually administered at a dose of 2.5 mg/kg, the dose of compound of formula (I) may vary between 0.75 mg/kg and 2.5 mg/kg, advantageously between 0.75 mg/kg and 2 mg/kg or even less.

Stated differently, the invention relates to a process for potentiating the antimicrobial activity of tulathromycin independently of the mechanism of resistance, comprising the following steps:
 a) Choosing a compound of formula (I) that is therapeutically inactive (as anti-infective) alone at the contemplated dose,
 b) Preparing a composition comprising the compound selected in step a) with tulathromycin.

The invention also relates to a method for treating and/or preventing a microbial infection in an animal, comprising co-administering tulathromycin and a compound of formula (I) to an animal suffering or likely to suffer from said microbial infection. The compound and tulathromycin are suitable for simultaneous, separate or staggered administration to the animal.

Surprisingly, it was shown that compounds of formula (I), used at this low concentration, are able to potentiate tulathromycin activity. Thus, the use of these potentiators advantageously allows tulathromycin to be used at a lower concentration, and/or at the usual concentration while having higher activity than tulathromycin alone at the same dose (increase in the intensity of the effect or in the kinetics of the effect).

In concrete terms, the invention notably makes it possible to:
 A/ decrease the doses at constant effect: decrease the amount of tulathromycin needed to inhibit/destroy usually sensitive microbes
 B/ increase the effect at constant dose: increase the ability of tulathromycin to inhibit/destroy sensitive germs (improvement in the kinetics of the effect, in the intensity of the effect, and broadening of the spectrum of activity of tulathromycin towards germs that were inconsistently sensitive or resistant to tulathromycin).

Reducing the administered dose (A/) of tulathromycin is of interest not only from the point of view of treating microbial infections in animals, notably the reduction of side effects, but also, and this is not negligible, from an environmental point of view (decreasing the development of resistance to tulathromycin). The use of tulathromycin at lower doses may help control the development of new mechanisms of resistance. In particular, tulathromycin may be used at a lower dose, wherein the tulathromycin dose administered is 1/50 to 3/4 of the tulathromycin dose necessary in the absence of co-administration of a compound according to invention for administration to an animal to treat microbial infections. Reducing the dose of tulathromycin at constant effect limits its toxicity. When applied to livestock, this reduces latency times before slaughter.

Increasing the effect of tulathromvycin at constant dose (B/) is of definite clinical interest both from a quantitative point of view, by improving the kinetics of an antimicrobial effect, and from a qualitative point of view, by making it possible to treat an animal suffering from a microbial infection with tulathromycin to which the strain was sensitive or inconsistently sensitive in the absence of potentiation. Increasing the speed of the effect of tulathromycin reduces the time the animal spends in the "infectious" state, thus reducing the epidemiology of the disease and the development and spread of resistance.

By virtue of the presence of compounds according to the invention, it is possible to increase the speed of bactericidal action of tulathromycin at constant dose of antimicrobial. Thus, the speed of action of potentiated tulathromycin can be increased.

By virtue of the presence of compounds according to the invention, the spectrum of tulathromycin can be broadened, notably at constant dose of tulathronmcin. Thus, tulathromycin potentiated by compounds according to invention can be used on strains that are no longer sensitive to tulathromycin in the absence of potentiation (notably due to the development of resistance).

In one embodiment, the compound of formula (I) is sufficient to potentiate tulathromycin, and consequently the use of a single compound of formula (I) is sufficient to potentiate tulathromycin. However, in certain cases, a combined use of inactive compounds may be contemplated.

In formula (I) $R_2$ and $R_3$ each represent H, $R_1$ represents a ($C_1$-$C_6$)alkyl group, and A represents the heteroatom O or an R—O—R' or —O—R' group, wherein R, R' each independently represent a ($C_1$-$C_2$)alkanediyl group optionally substituted by $C_1$-$C_4$ alkyl radicals.

Advantageously, the compound is of formula (Ia):

(Ia)

[Structural formula showing bicyclic compound with O-R' and $R_1, R_2, R_3$ substituents]

With $R_1$, $R_2$, $R_3$ and R' as defined above, in particular $R_2$ and $R_3$ each represent H, $R_1$ represents a ($C_1$-$C_6$)alkyl group. R' represents a ($C_1$-$C_2$)alkanediyl group. Advantageously the compound of formula (I) is cineole.

Within the scope of the present invention, the microbial infection is advantageously an infection induced by a pathogen selected from the following potentially pathogenic genera: *Acetobacter, Acetobacterium, Acinetobacter, Citro-* bacter, Enterobacter, Enterococcus, Escherichia, Helicobacter, Histophilus, Haemophilus, Klebsiella, Mycoplasma, Moraxella, Proteus, Providencia, Pseudomonas, Salmonella, Serratia, Staphylococcus, Streptococcus. Actinobacillus, Neisseria, Mannheimia, Pasteurella, Candida, Aspergillus, Cryptococcus, Trichosporon, Malassezia and Mycobacterium. In particular, a pathogen selected from the following potentially pathogenic genera: Mannheimia, Pasteurella, Histophilus, Mycoplasma, Moraxella, Actinobacillus, Haemophilus.

The bacterial strain or species is advantageously selected from the group consisting of: Acetobacter, Acetobacterium, Acinetobacter, Actinobacillus, Citrobacter, Enterobacter, Enterococcus. Escherichia, Helicobacter, Histophilus, Haemophilus, Klebsiella, Mannheimia, Mycoplasma, Moraxella, Pasteurella, Proteus, Providencia, Pseudomonas, Salmonella, Serratia, Staphylococcus and Streptococcus. More particularly, the bacterial strain or species is advantageously selected from the group consisting of Citrobacter freundii, Enterobacter aerogenes, Enterobacter cloacae, Escherichia coli, Klebsiella oxytoca, Klebsiella pneumoniae, Proteus mirabilis, Providencia stuartii, Salmonella sp., Serratia marcescens, Acinetobacter baumannii, Burkholderia cepacia, Pseudomonas aeruginosa, Staphylococcaceae, Staphylococcus aureus, Enierococcus faecium, Enterococcus sp., Mannheimia haemolytica, Pasteurella multocida, Histophilus somni, Mycoplasma bovis, Moraxella bovis, Actinobacillus pleuropneumoniae, Pasteurella multocida, Mycoplasma hyopneumoniae, Streptococcus suis and Haemophilus parasuis. Therefore, the bacterium can be either a Gram-negative bacterium or a Gram-positive bacterium.

The bacterium is more advantageously selected from the group consisting of Mannheimia haemolytica, Pasteurella multocida, Histophilus somni, Mycoplasma bovis. Moraxella bovis, Actinobacillus pleuropneumoniae, Pasteurella multocida, Mycoplasma hyopneumoniae, Streptococcus suis and Haemophilus parasuis.

The compounds according to the invention are advantageously administered systemically. They are therefore suitable for systemic administration.

The compounds according to the invention may be used in any pharmaceutical composition formulated so as to facilitate administration thereof. The pharmaceutical composition may comprise all commonly used pharmaceutically acceptable excipients such as carrier(s) or diluent(s).

The pharmaceutical composition may be administered via the oral, enteral, parenteral (intravenous, intramuscular or subcutaneous, intraperitoneal), transcutaneous (or transdermal or percutaneous), cutaneous or mucosal (especially transmucosal-buccal, nasal, ophthalmic, otologic, vaginal, rectal) routes, or via the intragastric, intracardiac, intraperitoneal, intrapulmonary or intratracheal routes.

The pharmaceutical composition may be in dry form, dry form to be reconstituted at the time of use (powder, lyophilizate, etc.), solid form (in particular cachet, powder, capsule, pill, granule, suppository, tablet, and more precisely fast-release tablet, gastro-resistant tablet or extended-release tablet), paste form (particularly gel, ointment, cream or pessary), liquid form (particularly syrup; injectable, infusible or oral solution; or eye drops), aerosol form (spray, vapour or gas), patch form, injectable form (in aqueous, non-aqueous or isotonic solution).

Furthermore, the pharmaceutical composition may be packaged for administration in the form of a single dose (monodose) or a multiple dose (multidose).

Tulathromycin and the compound(s) according to the invention may be administered in the same pharmaceutical composition or in separate pharmaceutical compositions, simultaneously, sequentially or spread over time. In the case of separate administration, the forms of the pharmaceutical compositions may be similar or different; the routes of administration may be identical or different.

The administration schedule will be adapted by the practitioner on a case by case basis. The routes of administration and the dosages vary as a function of a variety of parameters, for example as a function of the patient's condition, the type of infection and the severity of the infection to be treated.

The animal is preferably a mammal, in particular a human, a pet, a livestock animal (cow, sheep, goat).

The following examples illustrate the invention.

MIC measurement: The minimum inhibitory concentration measurement tests are performed in solid agar medium according to current international standards (CLSI standards), according to the protocol defined above. The compounds and compositions incorporated in the agar may be first diluted in one or more solvents (ethanol, or DMSO diluted in water).

The antibiotic is tulathromycin.

Unless otherwise indicated, the ratios in the tables are mass ratios.

Example 1: Measurement of Minimum Inhibitory Concentrations

The MIC of tulathronycin alone or in combination with cineole is shown in Tables 1 to 3 below.
In these tables, the following abbreviations are used:
ATB=tulathromycin
C=1,8-cineole
1/1: ATB/C mass ratio
X mg=fixed amount of X mg of cineole, the amount of tulathromycin varying as a function of the MIC
EtOH=ethanol

TABLE 1

| Reference | Name | ATB EtOH | ATB + C 1/1 EtOH | ATB DMSO | ATB + C 5 mg DMSO |
|---|---|---|---|---|---|
| 13030 | Actinobacillus pleuropneumoniae | 0.5 | 0.5 | 0.5 | 0.375 |
| 13032 | Actinobacillus pleuropneumoniae | 0.5 | 0.5 | 0.5 | 0.375 |
| 13041 | Actinobacillus pleuropneumoniae | 0.5 | 0.5 | 0.5 | 0.375 |
| 13042 | Actinobacillus pleuropneumoniae | 0.6 | 0.5 | 0.5 | 0.5 |
| 13043 | Actinobacillus pleuropneumoniae | 0.6 | 0.5 | 0.5 | 0.5 |
| 13045 | Actinobacillus pleuropneumoniae | 0.6 | 0.5 | 0.5 | 0.5 |
| 13012 | Actinobacillus pleuropneumoniae | 2 | 1.5 | 2 | 1.5 |
| 13120 | E. coli | 2.7 | 1.5 | 2 | 1.5 |
| 13121 | E. coli | 2.7 | 1.5 | 2 | 1.5 |
| 13122 | E. coli | 2 | 1.5 | 2 | 1.5 |
| 13123 | E. coli | 2 | 1.5 | 2 | 1.5 |
| 13124 | E. coli | 2 | 1.1 | 1.5 | 1.1 |
| 13125 | E. coli | 1.5 | 0.8 | 1.5 | 1.1 |
| 13126 | E. coli | 2 | 1.5 | 2 | 1.5 |
| 13128 | E. coli | 2 | 1.5 | 2 | 1.5 |
| 13129 | E. coli | 3.6 | 2.7 | 2.7 | 2 |
| 13130 | E. coli | 3.6 | 2 | 2 | 1.5 |
| 13131 | E. coli | 1.5 | 0.8 | 1.5 | 1.1 |
| 13132 | E. coli | 2.7 | 2 | 2 | 1.5 |
| 13133 | E. coli | 2 | 1.1 | 1.5 | 1.5 |

TABLE 1-continued

| Reference | Name | ATB EtOH | ATB + C 1/1 EtOH | ATB DMSO | ATB + C 5 mg DMSO |
|---|---|---|---|---|---|
| 13134 | E. coli | 1.5 | 1.1 | 1.5 | 1.1 |
| 13170 | E. coli | 2 | 1.1 | 1.5 | 1.1 |
| 13171 | E. coli | 3.6 | 2.7 | 2.7 | 2 |
| 13172 | E. coli | 1.5 | 1.1 | 1.5 | 0.8 |
| 13173 | E. coli | 1.5 | 1.1 | 1.5 | 1.1 |
| 13174 | E. coli | 2 | 1.5 | 2 | 1.5 |
| 13175 | E. coli | 3.6 | 2 | 2 | 2 |
| 13092 | Streptococcus suis | 1.1 | 0.5 | 1.1 | 0.6 |

TABLE 2

| Reference | Name | ATB EtOH | ATB + C 1/1 EtOH | ATB + C 1 mg EtOH |
|---|---|---|---|---|
| Q102CEA | E. coli | 1.42 | 0.8 | 0.8 |
| Q103IEA | E. coli | 1.42 | 1.06 | 0.8 |
| Q103JEA | E. coli | 1.42 | 1.06 | 0.8 |
| Q96IEB | E. coli | 1.42 | 1.42 | 1.07 |
| Q99IEA | E. coli | 1.42 | 0.8 | 0.8 |
| Q103I5 | E. coli | 1.42 | 0.8 | 0.8 |
| Q96CEB | E. coli | 1.9 | 1.42 | 1.07 |
| Q99JEA | E. coli | 1.42 | 0.8 | 0.8 |
| Q97IEA | E. coli | 1.42 | 1.06 | 0.8 |
|  | E. coli | 1.42 | 0.8 | 0.8 |
|  | E. coli | 1.42 | 0.8 | 0.8 |
| Q103CEA | E. coli | 1.42 | 1.06 | 0.8 |
| Q54IE2 | E. coli | 0.8 | 0.6 | 0.6 |
| Q96IEB | E. coli | 1.42 | 1.06 | 0.8 |
| Q99J1 | E. coli | 1.42 | 0.8 | 0.8 |
| Q97JEA | E. coli | 1.07 | 0.8 | 0.6 |
| 8152 | Enterococcus | 1 | 0.6 | 0.121 |
| 8153 | Enterococcus | 1.42 | 1.06 | 0.8 |
| 8146 | Staphylococcus | 0.45 | 0.34 | 0.121 |
| 8147 | Staphylococcus | 0.45 | 0.34 | 0.121 |
| 8148 | Staphylococcus | 0.45 | 0.34 | 0.121 |
| 8149 | Staphylococcus | 0.45 | 0.45 | 0.34 |
| 8238 | Staphylococcus | 0.45 | 0.34 | 0.34 |
| 12216 | Staphylococcus | 2.53 | 1.9 | 1.9 |
| 13218 | Staphylococcus | 1.07 | 0.6 | 0.121 |
| 13221 | Staphylococcus | 1.07 | 0.6 | 0.121 |

TABLE 3

| Name | ATB EtOH | ATB + C 1 mg EtOH | ATB + C 5 mg EtOH |
|---|---|---|---|
| Enterococcus | 0.9 | 0.9 | 0.7 |
| Enterococcus | 1.7 | 1.7 | 1.3 |

Cineole is shown to be able to potentiate tulathromycin on a large number of strains.

Example 2: Growth Test/Bactericidal Action Test

Growth tests are performed in liquid medium with prior dispersion of the antibiotic booster in a suitable solvent (here DMSO).

Bacterial growth kinetics are measured in the presence of tulathromycin (at a concentration of 4 or 16 times its MIC); tulathromycin (at a concentration of 4 or 16 times its MIC) and 1,8-cineole at a mass ratio of 1:1; and tulathromycin (at a concentration of 4 or 16 times its MIC) and 1 mg of 1,8-cineole.

MIC of tulathromycin=2 mg/L (strain 13120) and 0.5 mg/(strain 13043),

1 Growth Test on Strain 13120 (Genus E. coli)

The results are shown in FIG. 1, whose legend is:

diamond: control (bacteria alone in DMSO)

square: tulathromycin diluted in DMSO at a concentration of 4 times its MIC triangle: tulathromycin and cineole, diluted in DMSO, tulathromycin is at a concentration of 4 times its MIC, the tulathromycin/cineole mass ratio is 1:1

Cross (x): tulathromycin and cineole, diluted in DMSO, tulathromycin is at a concentration of 4 times its MIC, cineole at 1 mg/L The presence of cineole, at a very low dose, is shown to increase the bactericidal action of tulathromycin.

2 Growth Test on Strain 13043 (Actinobactllus Pleuropneumonlae)

Figure 2:
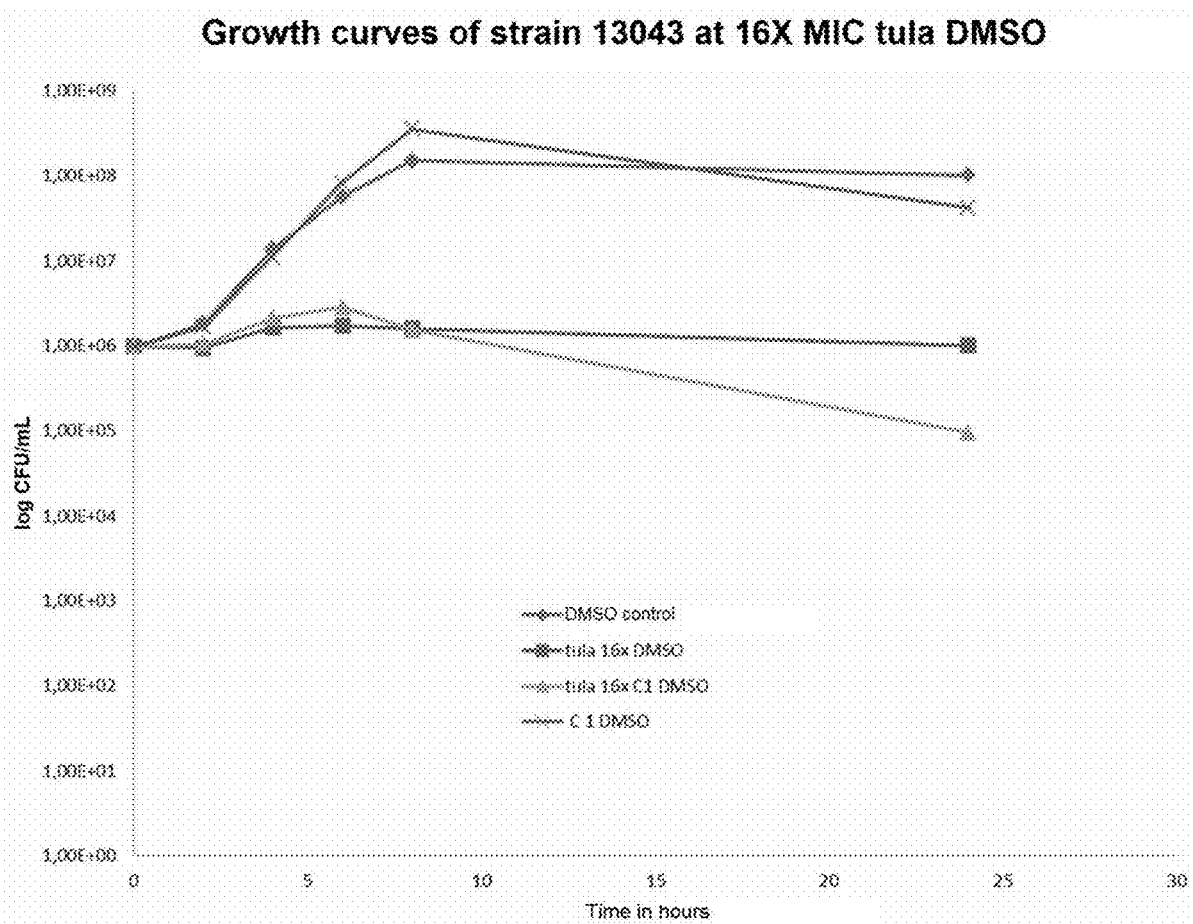
FIG. 2 is the results of the growth test on strain 13043 (*Actinobacillus pleuropneumonias*).

The results are shown in FIG. 2, whose legend is:

diamond: control (bacteria alone in DMSO)

square: tulathromycin diluted in DMSO at a concentration of 16 times its MIC triangle: tulathromycin and cineole, diluted in DMSO, tulathromycin is at a concentration of 16 times its MIC, cineole at 1 mg/L Cross (x): cineole control, at 1 mg/L The presence of cineole, at a very low dose, is shown to significantly decrease the number of bacteria while tulathromycin is a bacteriostatic antibiotic on this strain, when used alone.

Example 3: Resistance

One hundred microlitres of a Mueller Hinton broth culture of the strain to be studied (heavy inoculum>$10^{10}$ CFU/mL) is spread on a Mueller Hinton plate containing an oil concentration equal to 0.5/1/2/4 times the MIC of tulathromycin. After 48 hours of incubation, the presence or absence of colonies likely to be resistant mutants are observed.

The use of cineole was also shown to reduce the development of resistant bacteria. The results are shown in the following tables:

TABLE 4

| Strain 8147/Staphylococcus - ethanol solvent | | | | |
|---|---|---|---|---|
| MIC | 4 | 2 | 1 | 0.5 |
| Tulathromycin | overgrown | overgrown | overgrown | overgrown |
| Tulathromycin + 1 mg/L cineole | overgrown | overgrown | overgrown | overgrown |
| Tulathromycin + 5 mg/L cineole | 0 | 0 | overgrown | overgrown |

Whereas tulathromycin alone on S. aureus causes countless mutants to develop, the addition of cineole (5 mg/L) to tulathromycin no longer causes mutants to develop.

TABLE 5

| Strain 8146/*Staphylococcus* - ethanol solvent | | | | |
|---|---|---|---|---|
| MIC | 4 | 2 | 1 | 0.5 |
| Tulathromycin | 0 | overgrown | overgrown | overgrown |
| Tulathromycin + 1 mg/L cineole | 0 | 2 colonies | overgrown | overgrown |
| Tulathromycin + 5 mg/L cineole | 0 | 1 colony | overgrown | overgrown |

Here again, cineole decreases the development of mutants.

The invention claimed is:

1. A method for treating a microbial infection in an animal, in need thereof, comprising co-administering tulathromycin and cineole; with a cineole:tulathromycin mass ratio varying from 8:1 to 1:10, and wherein the microbial infection is induced by a microbial pathogen and the concentration of cineole ([C]) is <[MIC]/x where [MIC] is the minimal inhibitory concentration measured for cineole alone, for the microbial pathogen and x is from 100 to 10,000.

2. The method according to claim 1, wherein x is greater than 1000.

3. The method according to claim 1, wherein x is between 2000 and 10,000.

4. The method according to claim 1, wherein the cineole: tulathromycin mass ratio varies from 4:1 to 1:10.

5. The method according to claim 1, wherein the cineole: tulathromycin mass ratio varies from 1:1 to 1:10.

6. The method according to claim 1, wherein the cineole: tulathromycin mass ratio varies from 1:1 to 1:5.

7. The method according to claim 1, wherein the dose of cineole is between 0.01 and 64 mg/kg.

8. The method according to claim 1, wherein the dose of cineole is between 0.1 and 30 mg/kg.

9. The method according to claim 7, wherein the dose of cineole is between 0.5 and 10 mg/kg.

10. The method according to claim 1, wherein the dose of tulathromycin is between 0.01 and 64 mg/kg.

11. The method according to claim 1, wherein the dose of tulathromycin is between 0.1 and 30 mg/kg.

12. The method according to claim 10, wherein the dose of tulathromycin is between 0.5 and 10 mg/kg.

13. The method according to claim 1, wherein tulathromycin is administered at a dose of 2.5 mg/kg, and the dose of cineole varies between 0.75 mg/kg and 2.5 mg/kg.

14. The method according to claim 13, wherein the dose of cineole varies between 0.75 mg/kg and 2 mg/kg.

15. The method according to claim 1, wherein the cineole is adapted for systemic administration.

16. A method for metaphylaxis of a microbial infection in an animal, in need thereof, comprising coadministering tulathromycin and cineole; with a cineole: tulathromycin mass ratio varying from 8:1 to 1:10, and wherein the microbial infection is induced by a microbial pathogen and the concentration of cineole ([C]) is <[MIC]/x where [MIC] is the minimal inhibitory concentration measured for cineole alone, for the microbial pathogen and x is from 100 to 10,000.

* * * * *